US00PP20916P2

(12) United States Plant Patent
Henny et al.

(10) Patent No.: US PP20,916 P2
(45) Date of Patent: Apr. 6, 2010

(54) ***PHILODENDRON* PLANT NAMED 'UFM1'**

(50) Latin Name: *Philodendron scandens oxycardium*
Varietal Denomination: UFM1

(75) Inventors: Richard Henny, Tavares, FL (US); Jianjun Chen, Apopka, FL (US)

(73) Assignee: Florida Foundation Seed Producers, Inc., Greenwood, FL (US)

( * ) Notice: Subject to any disclaimer, the term of this patent is extended or adjusted under 35 U.S.C. 154(b) by 0 days.

(21) Appl. No.: 12/315,708

(22) Filed: Dec. 4, 2008

(51) Int. Cl.
*A01H 5/00* (2006.01)

(52) U.S. Cl. ..... Plt./381

(58) Field of Classification Search ..... Plt./381
See application file for complete search history.

*Primary Examiner*—Susan B McCormick Ewoldt

(57) ABSTRACT

A new *Philodendron* plant particularly distinguished by having very small, narrow green leaves, compact vines with short internodes and dense growth habit, and vines that produce lateral branches, is disclosed.

2 Drawing Sheets

ACKNOWLEDGEMENT OF FEDERAL RESEARCH SUPPORT

This invention was made with government support under FLA-APO-04158 awarded by the Cooperative State Research, Education, and Extension Service, USDA. The government has certain rights in the invention.

Genus and species: *Philodendron scandens oxycardium.*

Variety denomination: 'UFM1'.

BACKGROUND OF THE NEW PLANT

The invention relates to a new and distinct variety of *Philodendron scandens oxycardium* plant named 'UFM1'. 'UFM1' originated by exposing cuttings of *Philodendron scandens oxycardium,* not patented, to gamma-ray radiation in Gainesville, Fla. After treatment, the cuttings were grown in a controlled environment in Apopka, Fla. The inventors selected the new *Philodendron* approximately 1 year later as a single branch mutation within the population of treated plants.

Asexual reproduction of the new cultivar by tip cuttings in a controlled environment in Apopka, Fla. has shown that the unique features of this new *Philodendron* are stable and reproduced true to type in successive generations of asexual reproduction.

Plant Breeder's Rights for this cultivar have not been applied for. 'UFM1' has not been made publicly available more than one year prior to the filing of this application.

SUMMARY OF THE INVENTION

The cultivar 'UFM1' has not been observed under all possible environmental conditions. The phenotype may vary somewhat with variations in environment such as temperature and light intensity, without, however, any variance in genotype.

The following traits have been repeatedly observed and are determined to be the unique characteristics of 'UFM1'. These characteristics in combination distinguish 'UFM1' as a new and distinct cultivar of *Philodendron:*

1. Very small, narrow green leaves.
2. Compact vines with short internodes and dense growth habit.
3. Vines that produce lateral branches.

DESCRIPTION OF THE PHOTOGRAPHS

This new *Philodendron* plant is illustrated by the accompanying photographs which show the plant's overall appearance. These photographs show the colors as true as it is reasonably possible to obtain in colored reproductions of this type. Colors in the photographs may differ slightly from the color values cited in the detailed botanical description which accurately describe the colors of the new *Philodendron.*

DESCRIPTION OF THE NEW CULTIVAR

Figure 1:
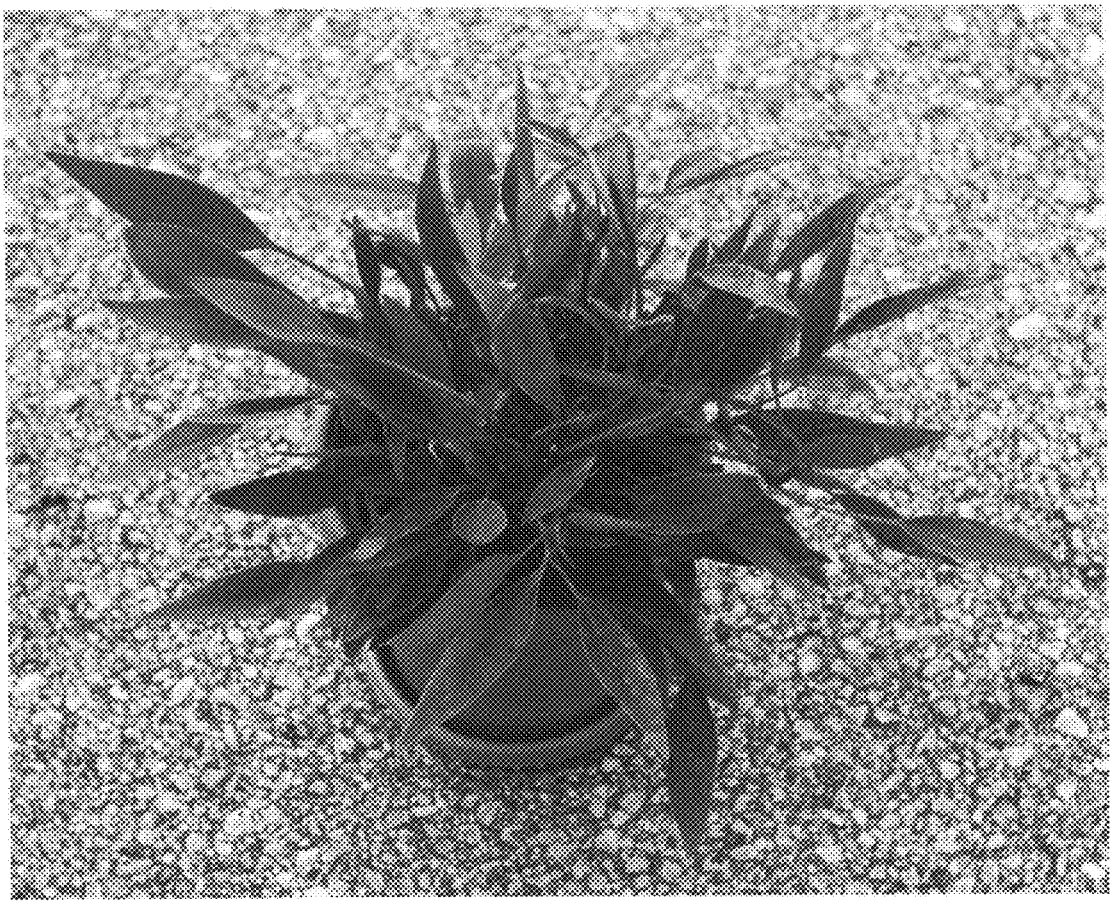
FIG. 1 shows a side perspective view of a typical plant of 'UFM1' grown for 12 weeks in a 10 cm diameter container.
Figure 2:
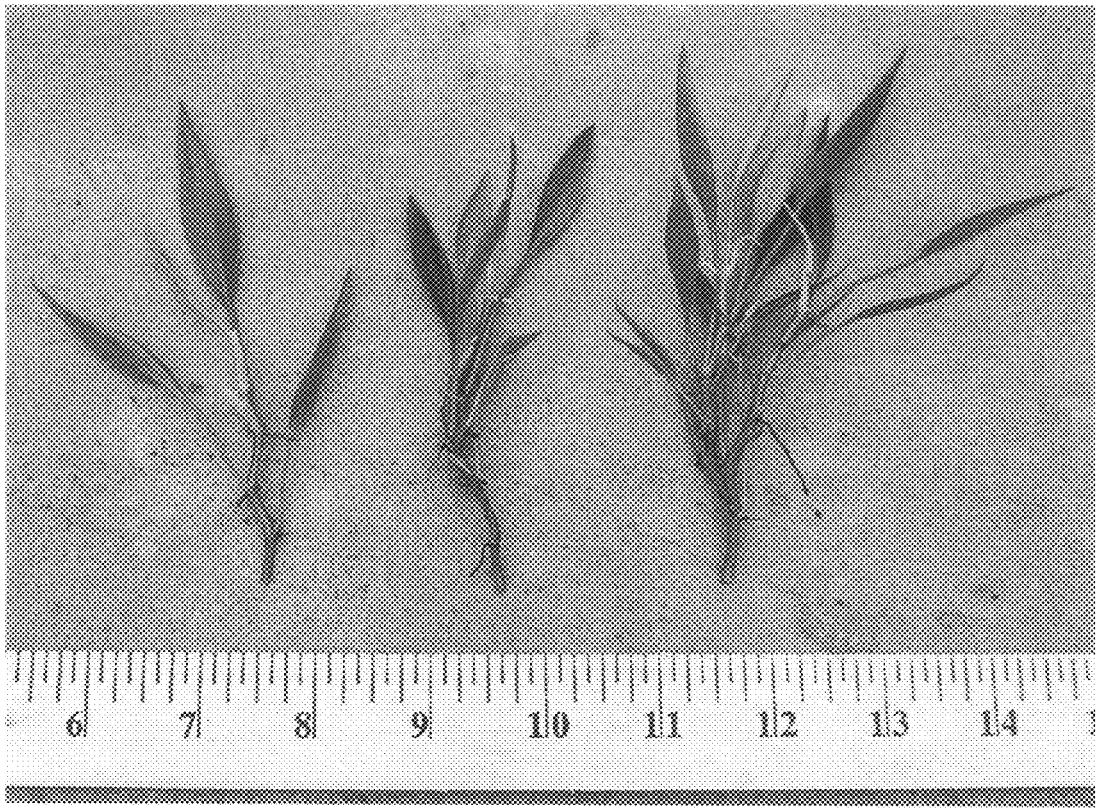
FIG. 2 shows a close-up view of typical vines and leaves of 'UFM1'.

The following detailed description sets forth the distinctive characteristics of 'UFM1' with color terminology in accordance with The Royal Horticultural Society Colour Chart, 2001 Edition, except where general terms of ordinary significance are used. The aforementioned photographs and following observations and measurements describe plants grown in containers in Apopka, Fla. during the spring and early summer in a glass-covered greenhouse. Plants were grown using practices and under conditions that approximate those generally used in commercial *Philodendron* production. During the production of the plants, day temperature ranged from about 29° C. to 35° C., night temperature ranged from a bout 18° C. to 26° C. and light levels were about 2,500 foot-candles. Plants were grown from single stem cuttings and were about 4 months old when the photographs and the detailed description were taken.

DETAILED BOTANICAL DESCRIPTION

Classification:

*Botanical.—Philodendron scandens oxycardium.*
*Common name.—Philodendron.*

Parentage: *Philodendron scandens oxycardium* (not patented).

Propagation:

*Type.*—By tip cuttings.

*Time to initiate roots, summer.*—About 20–25 days at 25° C. to 35° C.

*Time to initiate roots, winter.*—About 21–28 days at 15° C. to 30° C.

*Time to produce a rooted young plant, summer.*—About 35 days at 25° C. to 35° C.

*Time to produce a rooted young plant, winter.*—About 21–28 days at 15° C. to 30° C.

*Root description.*—Medium thick, fleshy; typical of species.

Plant description:

*Plant/growth habit.*—Low growing, trailing. Plants are full, compact and have dense foliage.

*Plant height, from soil level to top of leaf plane.*—8–10 cm.

*Crop time.*—From sticking 10 unrooted cuttings per container, about 12 to 16 weeks are required to produce finished plants in 10 cm containers.

*Plant diameter or spread.*—About 20 to28 cm.

*Stem description.*—Length: About 20 to 25 cm. Diameter: About 2 to 3 mm. Internode length: About 1 to 3 cm. Texture: smooth. Branching: stems tend to produce several secondary branches naturally. Color, immature: 147B/C. Color, mature: 137 A/C.

Foliage description:

*Leaves.*—Arrangement: alternate. Length: About 5 to 7 cm. Width: About 1.5 to 2.0 cm. Shape: Sharply lanceolate. Apex: Acuminate. Base: Attenuate. Aspect: Mostly flat. Margin: Entire. Texture, upper and lower surfaces: smooth. Color immature expanding leaves upper surface: 147B/C; lower surface 147B/C. Color mature leaves upper surface: 137A; lower surface 137C.

*Petiole.*—Length: About 3 to 5 cm. Diameter: About 1 to 1.5 mm. Color: 137C.

Inflorescence description: Inflorescence development has not been observed on plants of the new *Philodendron.*

Disease resistance: Resistance to pathogens common to *Philodendron* has not been observed on plants of the new *Philodendron.*

COMPARISON WITH PARENTAL AND KNOWN CULTIVARS

'UFM1' differs from plants of the parent, the species *oxycardium,* in the following characteristics:

1. 'UFM1' has leaves that are much smaller and narrower than leaves of the parent plant.
2. 'UFM1' has leaves that are completely different in shape compared to leaves of the parent plant.
3. 'UFM1' has internodes that are much shorter compared to internodes of the parent plant.

Comparisons were made with the variety 'Brasil' (patented, U.S. Plant Pat. No. 12,956). In side-by-side comparisons conducted in Apopka, Fla., plants of 'UFM1' differed from plants of the cultivar 'Brasil' in the following characteristics:

1. 'UFM1' has leaves that are much smaller and narrower compared to plants of the cultivar 'Brasil'.
2. 'UFM1' has leaves that are completely different in shape compared to leaves of the cultivar 'Brasil'.
3. 'UFM1' has leaves that are green compared to the cultivar 'Brasil' that has green and yellow green variegated leaves.

I claim:

1. A new and distinct cultivar of *Philodendron* plant named 'UFM1' as shown and described herein.

* * * * *